(12) United States Patent
Olsson et al.

(10) Patent No.: US 8,183,247 B2
(45) Date of Patent: May 22, 2012

(54) BORON COMPOUNDS USEFUL IN BNCT

(75) Inventors: Lars-Inge Olsson, Sodertalje (SE); Erwan Arzel, Ronninge (SE); Arne Eek, Trosa (SE)

(73) Assignee: Hammercap AB, Stockholm (SE)

( * ) Notice: Subject to any disclaimer, the term of this patent is extended or adjusted under 35 U.S.C. 154(b) by 1073 days.

(21) Appl. No.: 11/990,634

(22) PCT Filed: Aug. 17, 2006

(86) PCT No.: PCT/SE2006/000952
§ 371 (c)(1),
(2), (4) Date: Apr. 14, 2008

(87) PCT Pub. No.: WO2007/021234
PCT Pub. Date: Feb. 22, 2007

(65) Prior Publication Data
US 2009/0227539 A1    Sep. 10, 2009

(30) Foreign Application Priority Data

Aug. 19, 2005 (SE) ........................ 0501847
Aug. 30, 2005 (SE) ........................ 0501903

(51) Int. Cl.
*A01N 43/90* (2006.01)
*A61K 31/519* (2006.01)
*C07D 487/00* (2006.01)

(52) U.S. Cl. ................. 514/262.1; 544/256; 544/257

(58) Field of Classification Search ............... 544/256, 544/257, 262.1; 514/262.1
See application file for complete search history.

(56) References Cited

U.S. PATENT DOCUMENTS
2004/0102417 A1   5/2004  Kagechika

FOREIGN PATENT DOCUMENTS

| EP | 1 113 020 A2 | 7/2001 |
| RU | 2003 127 114 A | 3/2005 |
| WO | WO-94/01440 A2 | 1/1994 |
| WO | WO-99/59640 A1 | 11/1999 |
| WO | WO-00/45857 A2 | 10/2000 |
| WO | WO 02/064601 A1 | 8/2002 |

OTHER PUBLICATIONS

Vippagunta et al., "Crystalline Solids", Adv. Drug Del. Rev., 48 (2001) 3-26.*
Shuka et al, Bioconjugate Chemistry (2003), 14(1), 158-167.*
Shukla S. et al., Bioconjugate Chemistry (2003), vol. 14, No. 1, pp. 158-167.
Pan X.Q. et al., Bioconjugate Chemistry (2002), vol. 13, No. 3, pp. 435-442.
Mathias C.J. et al., Nuclear Medicine and Biology (2003), vol. 30, No. 7, pp. 725-731.
Leamon et al., Advanced Drug Delivery Reviews, 56 (2004), pp. 1127-1141.
H. P. C. Hogenkamp et al., Nuclear Medicine and Biology (2000), 27, pp. 89-92.

* cited by examiner

*Primary Examiner* — Paul V. Ward
(74) *Attorney, Agent, or Firm* — Birch, Stewart, Kolasch & Birch, LLP

(57) ABSTRACT

The present invention relates to novel boron comprising compounds, to pharmaceutical compositions comprising said compounds, to the therapeutic use of said compounds, and to a process for preparation of said compounds. The compounds are useful in boron neutron capture therapy (BNCT).

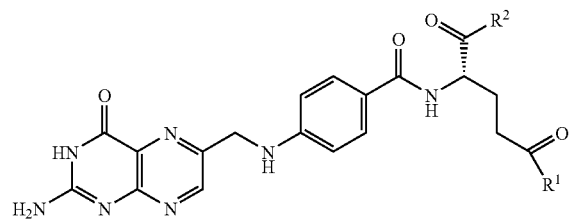

16 Claims, No Drawings

BORON COMPOUNDS USEFUL IN BNCT

TECHNICAL FIELD

The present invention relates to novel boron-comprising compounds, to pharmaceutical compositions comprising said compounds, to the therapeutic use of said compounds, and to a process for preparation of said compounds.

BACKGROUND ART

Boron neutron capture therapy (BNCT) is a form of radiation therapy requiring two components: $^{10}$B and low energy thermal neutrons. The $^{10}$B is administered to the subject to be treated in the form of a boron-containing compound that accumulates in the tumour. The subject to be treated is then irradiated with low energy thermal neutrons from a nuclear reactor or cyclotron.

When low energy thermal neutrons hit $^{10}$B, they generate an α-particle and $^7$Li. The thermal neutrons have a relatively low energy. However, upon generation of $^7$Li and an α-particle, sufficient energy to destroy a cell is generated. Since the α-particle and $^7$Li are relatively large, they are only transported about 5-10 μm in the tissue, i.e. a distance corresponding to the diameter of a tumour cell. Thus, BNCT can be used to selectively irradiate tumours while minimizing the radiation damage to non-malignant tissue.

A major challenge in BNCT is to find a non-toxic carrier molecule for the boron atom that will concentrate in the cells of the tumour to ensure sufficient selectivity. Such compounds should preferably deliver average $^{10}$B concentrations of 15-30 μg/g (ppm, i.e. parts per million) in tumours with high selectivity (tumour-to-blood and tumour-to-normal tissues ratios ideally>5) and with low toxicity, in order to attain a high therapeutic ratio. One approach has been to use boron-containing nucleosides, nucleotides or oligonucleotides (EP 1 113 020 A2). Another approach has been the use of nucleosides and oligonucleotides comprising a boronated phosphoramidate (WO 94/01440 A1). Further, carboranyl pyrimidines have been prepared for use in BNCT. Purine and pyrimidine nucleosides containing a carboranyl group attached to the purine or pyrimidine base have also been reported. The synthesis of nidocarborane-cobalamin conjugates that could be useful in neutron capture therapy has also been performed (H. P. C. Hogenkamp et al., *Nuclear Medicine and Biology* (2000), 27, 89-92).

Two boron neutron capture agents currently in phase I/II clinical trials are disodium mercapto-closo-dodecaborate (BSH) and 1-4-dihydroxyborylphenylalanine (BPA). Although BSH and BPA have been shown to be safe and efficacious in animal models, both of these agents have only moderate selectivity for tumour cells and low retention times in tumours. Furthermore, BSH has limited chemical stability due to its tendency toward air-oxidation, and BPA, although chemically non-toxic, contains only a low percent of boron by weight (5%) so that large amounts of this drug are needed in order to achieve therapeutic boron concentrations in tumour tissue.

Leamon, C. P. and Reddy, J. A., *Advanced Drug Delivery Reviews*, 56 (2004) 1127-1141, discusses the folate receptor and folate-drug conjugates for therapeutic purposes.

WO 00/45857 discloses the use of a physiologically compatible compound constituted by a Gd$^{3+}$ complex moiety and a tumour specific moiety of biological or synthetic origin, for producing preparations for neutron capture and photon activation therapy.

SUMMARY OF THE INVENTION

An object of the present invention is to provide compounds useful in boron neutron capture therapy (BNCT).

Another object is to provide such compounds having a high level of boron by weight and/or being selective for tumour cells. Another object is to provide such compounds being stable and/or non-toxic.

Still another object of the present invention is to provide pharmaceutical compositions comprising said compounds and to provide for the use of said compounds in therapy.

A further object is to provide a process for the preparation of said compounds from known starting materials.

The above-mentioned objects as well as other objects of the invention, which should be apparent to a person skilled in the art after having studied the description below, are accomplished by a compound according to formula (I)

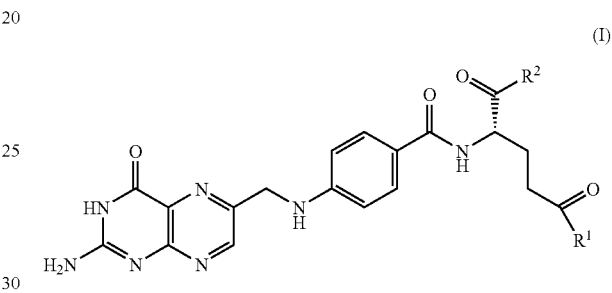

(I)

wherein
one of R$^1$ and R$^2$ is —NH—X—Y—Z, —O—X—Y—Z or —S—X—Y—Z, and the other is —OH, —NH—X—Y—Z, —O—X—Y—Z or —S—X—Y—Z;
wherein
X is —(CH$_2$)$_n$—, wherein m is 0, 1, 2, 3 or 4, or —(CH$_2$)$_p$—O—(CH$_2$)$_q$—, wherein p and q independently are 1, 2, 3 or 4;
Y is a borane or a carborane, wherein at least one boron atom is $^{10}$B; and
Z is H or a hydrophilizing group, such as aminomethyl, 2-aminoethyl, 3-aminopropyl, 1,3-propanediol-2-ylmethoxyl, ethyleneglycoxyl or diethyleneglycoxyl;
and pharmaceutically acceptable salts, solvates and stereoisomers thereof.

Preferably, the abundance of $^{10}$B in the borane or carborane of Y is higher than the natural isotopic abundance of $^{10}$B. For example, more than 10% or more than 20%, preferably more than 25%, more preferably more than 50% or more than 75%, of the boron atoms present in the borane or carborane of Y may be $^{10}$B.

The compounds according to formula (I) may be in the form of a pharmaceutically acceptable salt. Such salts are for example salts formed with mineral acids such as hydrochloric acid; ammonium salts formed with amines, such as triethylamine or a basic drug; alkali metal salts such as sodium or potassium salts; or alkaline earth metal salts such as calcium or magnesium salts.

The compounds according to formula (I) may be in the form of pharmaceutically acceptable solvates, for example hydrated, as well as in unsolvated forms.

When one or more stereocenter is present in the molecule, the compounds according to formula (I) may be in the form of a pharmaceutically acceptable stereoisomeric mixture, e.g. a mixture of diastereomers and/or a mixture of enantiomers. Diastereomers are stereoisomers whose molecules are not mirror images of each other. Enantiomers are stereoisomers whose molecules are mirror images of each other. Further, the compounds according to formula (I) may be in the form of a pharmaceutically acceptable single stereoisomer, i.e. a single enantiomer and/or diastereomer. The compounds according to formula (I) may also be in the form of a pharmaceutically acceptable racemic mixture, i.e. an equimolar mixture of enantiomers.

Borane is defined herein as a polyhedral borane, see *Gmelin Handbook of Inorganic and Organometallic Chemistry* (8th ed. 1991). Carborane is defined herein as a compound wherein at least one carbon atom is incorporated into a polyhedral borane. Carboranes can be synthesised according to descriptions in Carboranes (R. Grimes ed. 1970), *Gmelin Handbook of Inorganic and organometallic Chemistry* (8th ed. 1991) and Science 1972, 78, 462.

The compounds according to formula (I) are useful in BNCT. Compounds according to formula (I) comprise a folic acid moiety, i.e. a significant part of the folic acid molecule. Said compounds further comprise a boron-containing moiety, and optionally a linker. The linker is defined as a moiety located between the folic acid moiety and the boron-containing moiety. The boron-containing moiety is defined as a group containing boron, and can be a borane or a carborane. Fast-growing cells such as tumour cells show an increased uptake of folic acid and structurally related compounds.

BNCT can be used for the therapy of a wide range of tumours. Tumours can be classified histologically according to principles defined by the World Health Organization (World Health Organization, *International Histological Classification of Tumours*, 1967-1978). Tumour types that can be treated using BNCT with the compounds according to formula (I) above include tumours originating from the central nervous system, preferably glioma such as glioblastoma, gliosarcoma, anaplastic astrocytoma, low grade astrocytoma, pilolytic astrocytoma, oligodendroglioma or brain stem glioma; meningioma; peripheral neuroepithelioma; primitive neuroectodermal tumour; neuroblastoma; germinoma; pituitary tumour; metastatic brain tumour; or arteriovenous malformation. The compounds according to formula (I) may also be used in BNCT for therapy of i.a. malignant tumours or metastatic tumour processes, preferably melanoma, prostate cancer, hepatic cancer, lung cancer, breast cancer or sarcoma.

The wording "boron neutron capture therapy" (BNCT) as used herein is defined as a method for tumour therapy comprising the steps of administering a boron-containing compound to a subject to be subjected to therapy and irradiating said subject with thermal neutrons.

The term "tumour" as used herein is defined in accordance with *Dorland's Illustrated Medical Dictionary*, 26th edition, 1985, Saunders, i.e. as a growth of tissue in which the multiplication of cells is uncontrolled and progressive. Uncontrolled multiplication is defined as a state differing from the normal multiplication of cells, e.g. a state in which the rate of multiplication of cells is significantly increased. The term "progressive" in this context is defined as advancing or increasing in severity. A tumour cell is defined as a cell in said tissue.

The term "therapy" as used herein is defined in accordance with *Dorland's Illustrated Medical Dictionary*, 26th edition, 1985, Saunders, i.e. as the treatment of disease. The terms "therapeutic" and "therapeutically" should be construed accordingly. The wording "tumour therapy" as used herein is thus defined as treatment of disease caused by or associated with a tumour.

The borane or carborane constituting Y of formula (I) may be

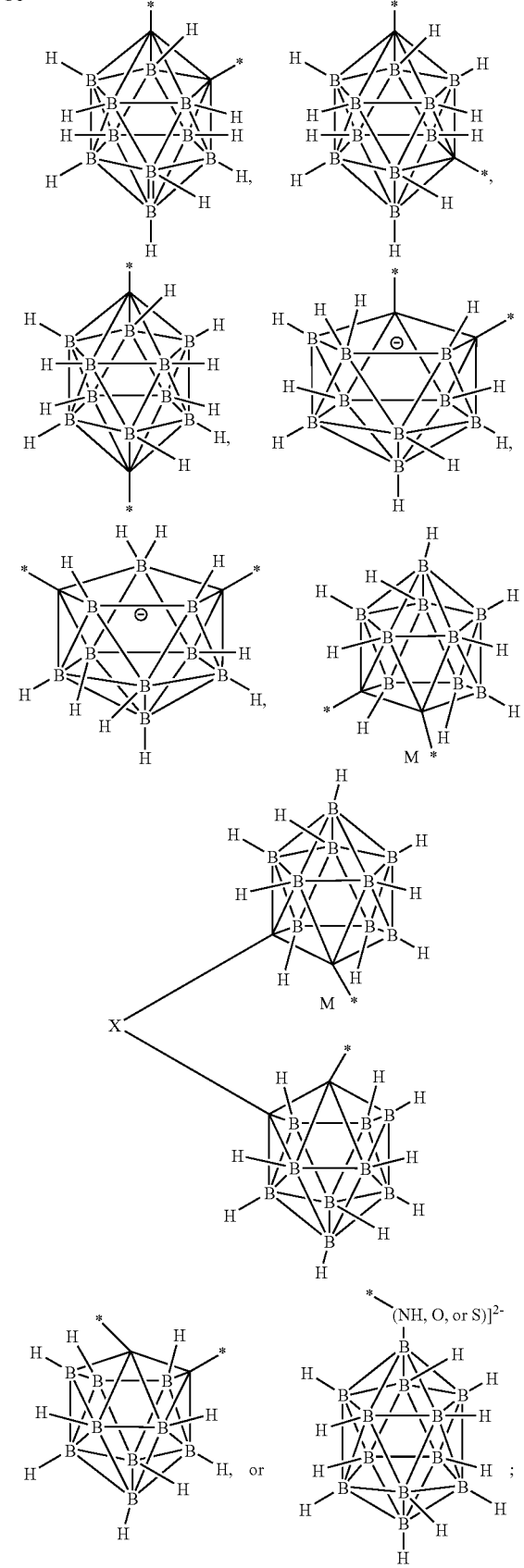

wherein
* indicates a location of a bond to X or Z;
M is cobalt, cobalt-57 or iron; and
X is as defined above.

Examples of compounds according to formula (I) are $N^2$-(4-{[(2-amino-4-oxo-3,4-dihydropteridin-6-yl)methyl]amino}benzoyl)-N-{3-[(1R,9S)-2,3,4,5,6,7,8,10,11,12-decaborabicyclo[7.2.1]dodec-1-yl]propyl}-α-glutamine and $N^2$-(4-{[(2-amino-4-oxo-3,4-dihydropteridin-6-yl)methyl]amino}benzoyl)-N-[3-(2,3,4,5,6,7,8,10,11,12-decaborabicyclo[7.2.1]dodec-1-yl)propyl]-L-glutamine.

In one embodiment, in the compound according to formula (I), $R^1$ is —NH—X—Y—Z, —O—X—Y—Z or —S—X—Y—Z, and $R^2$ is OH. Such a compound closely resembles the structure of folic acid and can thus retain all or part of the biological activities shown by folic acid.

In one embodiment, in the compound according to formula (I), at least one carbon atom is $^{11}C$. Such an embodiment allows detection of the compound by positron emission tomography (PET) techniques.

Alternatively, the Y moiety of a compound of formula (I) may be a gadolinium-comprising entity.

The objects of the present invention are further accomplished by a process for the preparation of a compound according to formula (I) wherein a compound of formula $NH_2$—X—Y—Z, OH—X—Y—Z or SH—X—Y—Z, wherein X, Y and Z are as defined in relation to formula (I), is reacted with folic acid.

Pharmaceutical Formulations

The objects of the present invention are also accomplished by a pharmaceutical composition comprising a compound according to formula (I) and a pharmaceutically acceptable carrier, diluent or adjuvant.

For clinical use, the boron-containing compounds according to formula (I) are in accordance with the present invention suitably formulated into pharmaceutical compositions for parenteral administration. Also rectal, oral or any other route of administration may be contemplated by the skilled man in the art of formulations. Thus, the boron-containing compounds according to formula (I) are formulated with at least one pharmaceutically and pharmacologically acceptable carrier or adjuvant. The carrier may be in the form of a solid, semi-solid or liquid diluent.

Solutions for parenteral administration may be prepared as a solution of a compound of the invention in a pharmaceutically acceptable solvent. These solutions may also contain stabilizing ingredients and/or buffering ingredients and are dispensed into unit doses in the form of ampoules or vials. Solutions for parenteral administration may also be prepared as a dry preparation to be reconstituted with a suitable solvent extemporaneously before use.

In the preparation of oral pharmaceutical compositions in accordance with the invention, the boron-containing compound(s) according to formula (I) to be formulated is/are mixed with solid, powdered ingredients such as lactose, saccharose, sorbitol, mannitol, starch, amylopectin, cellulose derivatives, gelatin, or another suitable ingredient, as well as with disintegrating agents and lubricating agents such as magnesium stearate, calcium stearate, sodium stearyl fumarate and polyethylene glycol waxes. The mixture is then processed into granules or compressed into tablets.

Soft gelatine capsules may be prepared with capsules containing a mixture of the active compound or compounds of the invention, vegetable oil, fat, or other suitable vehicle for soft gelatine capsules. Hard gelatine capsules may contain the active compound in combination with solid powdered ingredients such as lactose, saccharose, sorbitol, mannitol, potato starch, corn starch, amylopectin, cellulose derivatives or gelatine.

Dosage units for rectal administration may be prepared (i) in the form of suppositories which contain the active substance(s) mixed with a neutral fat base; (ii) in the form of a gelatine rectal capsule which contains the active substance in a mixture with a vegetable oil, paraffin oil, or other suitable vehicle for gelatine rectal capsules; (iii) in the form of a ready-made micro enema; or (iv) in the form of a dry micro enema formulation to be reconstituted in a suitable solvent just prior to administration.

Liquid preparations for oral administration may be prepared in the form of syrups or suspensions, e.g. solutions or suspensions, containing the active compound and the remainder of the formulation consisting of sugar or sugar alcohols, and a mixture of ethanol, water, glycerol, propylene glycol and polyethylene glycol. If desired, such liquid preparations may contain colouring agents, flavouring agents, saccharine and carboxymethyl cellulose or other thickening agent. Liquid preparations for oral administration may also be prepared in the form of a dry powder to be reconstituted with a suitable solvent prior to use.

In one aspect of the present invention, the boron-containing compound according to formula (I) may be administered within 24 hours prior to the neutron irradiation of the subject to be treated, typically 30-60 minutes prior to neutron irradiation. In a further aspect of the invention the dosage of the boron-containing compound may be in pulses. A typical dose of the boron-containing compound according to formula (I) is within the range of from 0.01-100 mg per kg body weight.

Therapies

The objects of the present invention are also accomplished by a compound according to formula (I) for use in therapy, or by the use of a compound according to formula (I) for the manufacture of a medicament for use in tumour therapy.

In on embodiment, the medicament may be for therapy of tumours originating from the central nervous system, preferably glioma such as glioblastoma, gliosarcoma, anaplastic astrocytoma, low grade astrocytoma, pilolytic astrocytoma, oligodendroglioma or brain stem glioma; meningioma; peripheral neuroepithelioma; primitive neuroectodermal tumour; neuroblastoma; germinoma; pituitary tumour; metastatic brain tumour; or arteriovenous malformation.

Alternatively, the medicament may be for therapy of malignant tumours or metastatic tumour processes, preferably melanoma, prostate cancer, hepatic cancer, lung cancer, breast cancer or sarcoma.

A useful embodiment of the present invention is also accomplished by a compound according to formula (I), wherein at least one carbon atom is $^{11}C$, for use in diagnostics, or by: the use of a compound according to formula (I), wherein at least one carbon atom is $^{11}C$, for the manufacture of a medicament for use in positron emission tomography (PET).

The objects are further accomplished by a method of tumour therapy wherein a pharmaceutically and pharmacologically effective amount of a compound according to formula (I) is administered to a subject in need of such treatment in conjunction with boron neutron capture therapy.

Said tumour therapy may be a therapy of tumours originating from the central nervous system, preferably glioma such as glioblastoma, gliosarcoma, anaplastic astrocytoma, low grade astrocytoma, pilolytic astrocytoma, oligodendroglioma or brain stem glioma; meningioma; peripheral neuroepithelioma; primitive neuroectodermal tumour; neuroblastoma; germinoma; pituitary tumour; metastatic brain tumour; or arteriovenous malformation.

Alternatively, said tumour therapy may be a therapy of malignant tumours or metastatic tumour processes, preferably melanoma, prostate cancer, hepatic cancer, lung cancer, breast cancer or sarcoma.

A useful embodiment of the present invention is further accomplished by a method of tumour diagnostics wherein a pharmaceutically and pharmacologically effective amount of a compound according to formula (I), wherein at least one carbon atom is $^{11}C$, is administered to a subject to be diagnosed in conjunction with positron emission tomography.

The therapies mentioned hereinbefore may be applied as a sole therapy or may involve, in addition to boron neutron capture therapy, conventional surgery or chemotherapy. Such chemotherapy may include one or more of the following categories of anti-tumour agents: (i) antiproliferative/antineoplastic drugs and combinations thereof, as used in medical oncology, such as alkylating agents (for example cis-platin, carboplatin, cyclophosphamide, nitrogen mustard, melphalan, chlorambucil, busulphan and nitrosoureas); antimetabolites (for example antifolates such as fluoropyrimidines like 5-fluorouracil and tegafur, raltitrexed, methotrexate, cytosine arabinoside and hydroxyurea; antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere); and topoisomerase inhibitors (for example epipodophyllotoxins like etoposide and teniposide, amsacrine, topotecan and camptothecin);
(ii) cytostatic agents such as antioestrogens (for example tamoxifen, toremifene, raloxifene, droloxifene and iodoxyfene), oestrogen receptor down regulators (for example fulvestrant), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;
(iii) agents which inhibit cancer cell invasion (for example metalloproteinase inhibitors like marimastat and inhibitors of urokinase plasminogen activator receptor function);
(iv) inhibitors of growth factor function, for example such inhibitors include growth factor antibodies, growth factor receptor antibodies (for example the anti-erbb2 antibody trastuzumab [Herceptin™] and the anti-erbb1 antibody cetuximab), farnesyl transferase inhibitors, tyrosine kinase inhibitors and serine/threonine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib), N-(3-ethynylphenyl)-6,7-bis(2-methoxyethoxy) quinazolin-4-amine (erlotinib) and 6-acrylamido-N-(3-chloro-4-fluorophenyl)-7-(3-morpholinopropoxy)quinazolin-4-amine), for example inhibitors of the platelet-derived growth factor family and for example inhibitors of the hepatocyte growth factor family;
(v) antiangiogenic agents such as those which inhibit the effects of vascular endothelial growth factor, (for example the anti-vascular endothelial cell growth factor antibody bevacizumab [Avastin™], compounds such as those disclosed in International Patent Applications WO 97/22596, WO 97/30035, WO 97/32856 and WO 98/13354) and compounds that work by other mechanisms (for example linomide, inhibitors of integrin αvβ3 function and angiostatin);
(vi) vascular damaging agents such as Combretastatin A4 and compounds disclosed in International Patent Applications WO 99/02166, WO 00/40529, WO 00/41669, WO 01/92224, WO 02/04434 and WO 02/08213;
(vii) antisense therapies, for example those which are directed to the targets listed above, such as ISIS 2503, an anti-ras antisense;
(viii) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and
(ix) immunotherapy approaches, including for example ex-vivo and in-vivo approaches to increase the immunogenicity of patient tumour cells, such as transfection with cytokines-such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

EXAMPLES

Preparation of Compounds According to the Invention

All solvents used were of analytical grade and commercially available anhydrous solvents were routinely used for reactions. Reactions were typically run under an inert atmosphere of nitrogen or argon.

$^1H$ NMR spectra were recorded on a Varian Unity+ 400 NMR Spectrometer equipped with a 5 mm BBO probehead with Z-gradients, or a Varian Gemini 300 NMR spectrometer equipped with a 5 mm BBI probehead, or a Bruker Avance 400 NMR spectrometer equipped with a 60 μl dual inverse flow probehead with Z-gradients, or a Bruker DPX400 NMR spectrometer equipped with a 4-nucleus probehead equipped with Z-gradients. Unless specifically noted in the examples, spectra were recorded at 400 MHz for proton. The following reference signal was used: the middle line of $CDCl_3$ δ 7.26 ($^1H$).

Mass spectra were recorded on a Waters LCMS consisting of an Alliance 2795 (LC), Waters PDA 2996 and a ZQ single quadrupole mass spectrometer. The mass spectrometer was equipped with an electrospray ion source (ESI) operated in a positive or negative ion mode. The capillary voltage was 3 kV and the cone voltage was 30 V. The mass spectrometer was scanned between m/z 100-700 with a scan time of 0.3 s. Separations were performed on either Waters X-Terra MS C8 (3.5 μm, 50 or 100 mm×2.1 mm i.d.) or an ACE 3 AQ (100 mm×2.1 mm i.d.) obtained from ScantecLab. Flow rates were regulated to 1.0 or 0.3 ml/min, respectively. The column temperature was set to 40° C. A linear gradient was applied using a neutral or acidic mobile phase system, starting at 100% A (A: 10 mM $NH_4OAc$ in 5% MeCN, or 8 mM HCOOH in 5% MeCN) ending at 100% B (MeCN).

Alternatively, mass spectra were recorded on a Waters LCMS consisting of an Alliance 2690 Separations Module, Waters 2487 Dual 1 Absorbance Detector (220 and 254 nm) and a Waters ZQ single quadrupole mass spectrometer. The mass spectrometer was equipped with an electrospray ion source (ESI) operated in a positive or negative ion mode. The capillary voltage was 3 kV and cone voltage was 30 V. The mass spectrometer was scanned between m/z 97-800 with a scan time of 0.3 or 0.8 s. Separations were performed on a Chromolith Performance RP-18e (100×4.6 mm). A linear gradient was applied starting at 95% A (A: 0.1% HCOOH (aq.)) ending at 100% B (MeCN) in 5 minutes. Flow rate: 2.0 ml/min.

HPLC analyses were performed on an Agilent HP1000 system consisting of G1379A Micro Vacuum Degasser, G1312A Binary Pump, G1367A Well plate auto-sampler, G1316A Thermostatted Column Compartment and G1315B Diode Array Detector. Column: X-Terra MS, Waters, 3.0× 100 mm, 3.5 μm. The column temperature was set to 40° C. and the flow rate to 1.0 ml/min. The Diode Array Detector was scanned from 210-300 nm, step and peak width were set to 2 nm and 0.05 min, respectively. A linear gradient was applied, starting at 100% A (A: 10 mM $NH_4OAc$ in 5% MeCN) and ending at 100% B (B: MeCN), in 4 min.

A typical workup procedure after a reaction consisted of extraction of the product with a solvent such as ethyl acetate, washing with water, followed by drying of the organic phase over $MgSO_4$ or $Na_2SO_4$, filtration and concentration of the solution in vacuo.

Thin layer chromatography (TLC) was performed on Merck TLC-plates (Silica gel 60 $F_{254}$) and UV visualized the spots. Flash chromatography was performed on a Combi Flash® Companion™ using RediSep™ normal-phase flash columns. Typical solvents used for flash chromatography were mixtures of chloroform/methanol, dichloromethane/methanol, heptane/ethyl acetate, chloroform/methanol/$NH_3$ (aq.) and dichloromethane/methanol/$NH_3$ (aq.).

Preparative chromatography was run on a Waters autopurification HPLC with a diode array detector. Column: XTerra MS C8, 19×300 mm, 10 μm. Gradient with MeCN/0.1 M $NH_4OAc$ in 5% MeCN in MilliQ water, run from 20% to 60% MeCN, in 13 min. Flow rate: 20 ml/min. Alternatively, purification was achieved on a semi-preparative Shimadzu LC-8A HPLC with a Shimadzu SPD-10A UV-vis.-detector equipped with a Waters Symmetry® column (C18, 5 μm, 100 mm×19 mm). Gradient with MeCN/0.1% trifluoroacetic acid in MilliQ water, run from 5% to 100% MeCN in 15 min. Flow rate: 10 ml/min.

The following abbreviations have been used:
DMAP 4-dimethylaminopyridine;
DMF N,N-dimethylformamide;
EDC 1-ethyl-3-(3-dimethylaminopropyl)carbodiimide;
EtOAc ethyl acetate;
HCl hydrogen chloride;
$CH_2Cl_2$ dichloromethane;
$CDCl_3$ deuteriated chloroform;
Ether diethyl ether;
MeCN acetonitrile;
$Na_2CO_3$ sodium carbonate;
NaOH sodium hydroxide;
$Na_2SO_4$ sodium sulphate;
$QHSO_4$ tetrabutylammonium hydrogen sulphate;
r.t. room temperature.

Starting materials used were either available from commercial sources or prepared according to literature procedures and had experimental data in accordance with those reported.

Example 1

Preparation of di-tert-butyl[3-(2,3,4,5,6,7,8,10,11,12-decaborabicyclo[7.2.1]dodec-1-yl)propyl]imidodicarbonate

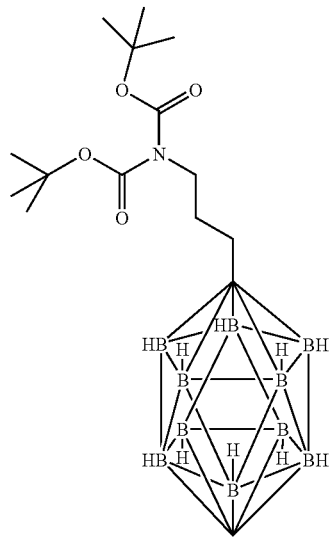

To a stirred mixture of $QHSO_4$ (3.04 g, 8.96 mmol) and NaOH 1 M aqueous solution (18 ml) was added $CH_2Cl_2$ (20 ml) followed by dropwise addition of 1-(3-bromopropyl)-2,3,4,5,6,7,8,10,11,12-decaborabicyclo[7.2.1]dodecane (*Tetrahedron Lett.* 1996, 37(38), 6905-6908) (2.16 g, 8.15 mmol) in $CH_2Cl_2$ (15 ml). The resulting solution was heated under reflux for 2 h and cooled to r.t. Water (10 ml) was added. The aqueous layer was extracted with $CH_2Cl_2$ (30 ml). The combined organic layers were washed with water (10 ml), dried over $Na_2SO_4$ and concentrated. The residue was stirred with ether (30 ml). The precipitate was extracted with dry ether (2×20 ml) and the combined extracts were concentrated under vacuum. The crude product was purified by flash chromatography.

Yield: 62% (2.21 g).

$^1$H NMR (400 MHz, $CDCl_3$): δ ppm 3.35 (t, 2H, J=7.07 Hz), 2.62 (s, 1H), 1.68-1.56 (m, 4H), 1.49-1.44 (m, 18H).

LC/MS (ESI) m/z 402 (M+1).

Example 2

Preparation of 3-(2,3,4,5,6,7,8,10,11,12-decaborabicyclo[7.2.1]dodec-1-yl)-propane-1-amine

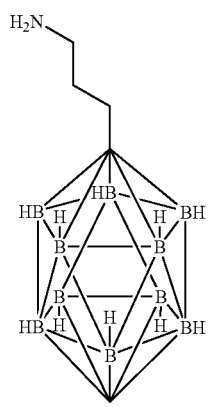

Di-tert-butyl[3-(2,3,4,5,6,7,8,10,11,12-decaborabicyclo[7.2.1]dodec-1-yl)propyl]imidodicarbonate from Example 1 (2.21 g, 5.50 mol) was dissolved in a saturated solution of HCl in EtOAc (100 ml). The solution was stirred overnight at r.t. and then evaporated. The white fluffy precipitate was washed with dry ether. The precipitate was then dissolved in water and the solution was basified with an aqueous saturated solution of $Na_2CO_3$ (40 ml). The aqueous layer was extracted with ether and the combined organic extracts were washed with brine (3×10 ml). Removing of the solvent under vacuum afforded the free amine.

Yield: 76% (841 mg).

$^1$H NMR (400 MHz, $CDCl_3$): δ ppm 2.62 (s, 1H) 2.54-2.42 (m, 2H), 1.69-1.58 (m, 2H), 1.44-1.33 (m, 2H).

LC/MS (ESI) m/z 202 (M+1).

Example 3

Preparation of $N^2$-(4-{[(2-amino-4-oxo-3,4-dihydropteridin-6-yl)methyl]amino}benzoyl)-N-{3-[(1R,9S)-2,3,4,5,6,7,8,10,11,12-decaborabicyclo[7.2.1]dodec-1-yl]propyl}-α-glutamine and $N^2$-(4-{[(2-amino-4-oxo-3,4-dihydropteridin-6-yl)methyl]amino}benzoyl)-N-[3-(2,3,4,5,6,7,8,10,11,12-decaborabicyclo[7.2.1]dodec-1-yl)propyl]-L-glutamine

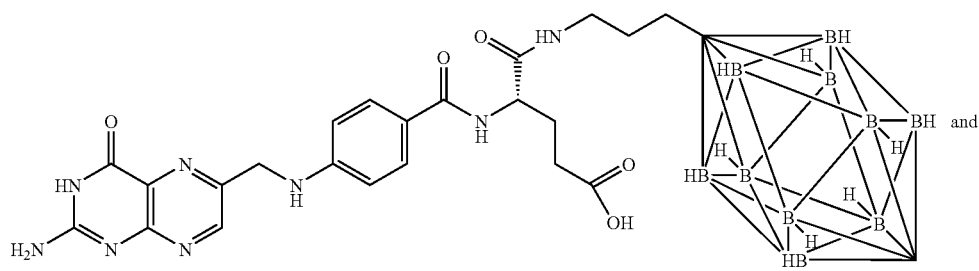 and

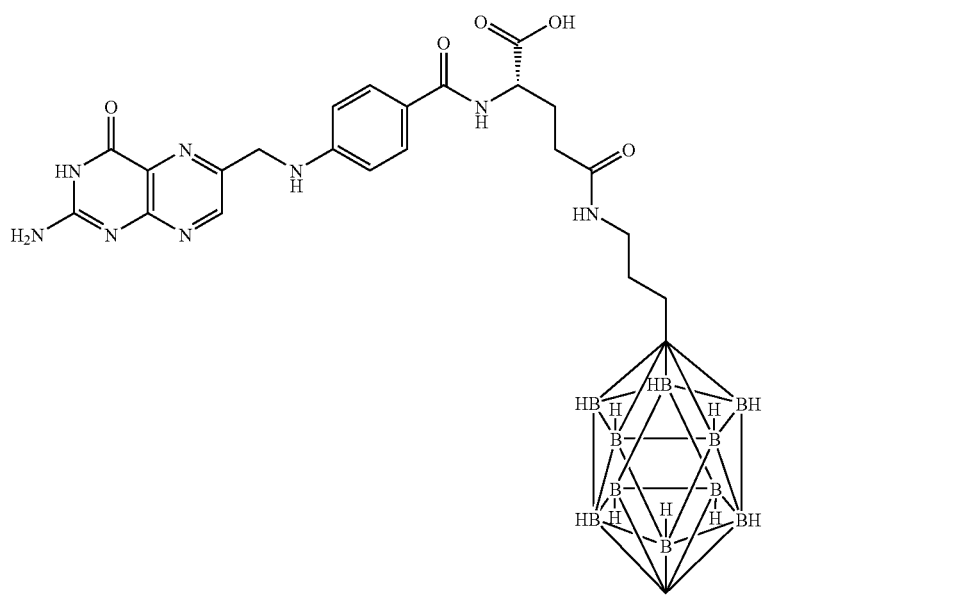

Folic acid (1.84 g, 4.17 mmol), EDC (799 mg, 4.17 mmol) and DMAP (509 mg, 4.17 mmol) were dissolved in dry DMF (200 ml). The solution was stirred for 3 h at 20° C. under argon atmosphere. Then a solution of 3-(2,3,4,5,6,7,8,10,11,12-decaborabicyclo[7.2.1]dodec-1-yl)-propane-1-amine from Example 2 (839 mg, 4.17 mmol) in DMF (40 ml) was added and the mixture was stirred for 1 day. The solvent was removed under vacuum. The residue was washed twice with a mixture ether/$CH_2Cl_2$. The crude material was purified by preparative HPLC.

Yield: 7.5% (190 mg).

LC/MS (ESI) m/z 623 (M−1) for both isomers. Retention time on a 12 min. method: 8.48 and 8.78 min. (an isocratic method was used in this case with a 2.5 mM aqueous solution of acetic acid).

In Vitro Studies of Compounds According to the Invention

Four different tumour cell lines of human origin, including human glioma cell line U343mga, human hepatocarcinoma cell line Hep3B, human breast adenocarcinoma cell line MCF7 and human sarcoma cell line 4SS, were used for in vitro testing of the purified material from Example 3 (hereinafter designated as BF). Cells were plated on non-coated tissue culture plastics and cultured at 37° C. in incubators with humidified air, equilibrated with 5% $CO_2$. They were grown in recommended tissue culture medium, supplemented with 10% FCS and PEST (penicillin 100 IU/ml and streptomycin 100 mg/ml). For passage of cells, cells were trypsinized with trypsin-EDTA (0.25% trypsin, 0.02% EDTA in phosphate buffered saline (PBS) without calcium and magnesium).

In summary, as will be shown below in Examples 4-6, BF has shown promising results in in vitro studies with superiority to BPA with respect to tumour cell uptake, accumulation and retention, without any signs of toxicity.

Example 4

Cell Uptake of BF

U343 mga cells were plated on Petri dishes at 75% cell density and incubated with one of boric acid (BA), vitamin $B_{12}$ conjugated boron (BB), 1-4-dihydroxyboryl-phenylalanine (BPA) or BF dissolved in tissue culture medium for 6 hours. All four boronated compounds were added to and dissolved in the tissue culture medium at equimolar concentrations with respect to the boron content ($5 \times 10^{-4}$ M boron). Incubations were stopped by removing the boron-containing tissue culture medium and by adding cold PBS buffer for washing excess of medium from cells. Cells were immediately harvested by scraping them off the plastic dish using a rubber policeman. They were collected in cold PBS and pelleted by centrifugation.

Cell samples were taken for total protein analysis according to a standard Bradford procedure. Cell pellets were processed for boron analysis by Direct Current Plasma-Atomic Emission Spectroscopy (DCP-AES). Samples (50-130 mg) were digested at 60° C. with sulfuric acid/nitric acid (1/1). Triton X-100 and water added to give a concentrations of 50 mg tissue/ml, 15% total acid v/v and 5% Triton X-100 v/v. The boron concentrations were based on a known reference sample.

The results are shown in Table 1 below. Covalent linkage of folate to boron in the form of BF results in active uptake into a human glioblastoma cell line U343 mga, that is superior to uptake of boron as boric acid (BA), boron-phenylalanine (BPA) or vitamin $B_{12}$ conjugated boron (BB).

TABLE 1

Cell uptake of different boronated compounds.

| Boronated compound | Trial 1 | Trial 2 |
|---|---|---|
| BA | 8 | — |
| BB | — | 60 |
| BPA | 65 | 38 |
| BF | 560 | 440 |

Boron content expressed as a function of total cell protein (μg boron/g cell protein) in U343mga cells for different boronated compounds in two parallel experiments (trial 1 and trial 2) (7.2 and 7.7 μg boron/ml culture medium in trial 1 and 2, respectively).

Example 5

BF Uptake by Different Tumor Cells

Four different tumor cell lines of human origin, U343 mga Hep3B, MCF7 and 4SS, were plated on Petri dishes at 40-50% (low) and 90-100% (high) cell density (confluency) and incubated with BF dissolved in tissue culture medium for 6 hours, as described. Incubations were stopped by removing the boron-containing medium and adding cold PBS buffer for washing excess of medium from cells. Cells were immediately harvested by scraping them of the plastic dish using a rubber policeman, collected in cold PBS and pelleted by centrifugation. Total protein and boron analysis were done according to standard procedures (see above).

The results are shown in Table 2 below. BF was found to be a highly efficient boron carrier in all four human tumour cell lines tested (glioblastoma (U343 mga), heptocarcinoma (Hep3B), breast cancer (MCF7), sarcoma (4SS)) at low and high cell density.

TABLE 2

Cell uptake of BF.

| Cell line | Low cell density | High cell density |
|---|---|---|
| U343mga | 108 | 172 |
| Hep3B | 171 | 219 |
| MCF7 | 108 | 169 |
| 4SS | 263 | 367 |

Boron content expressed as a function of total cell protein (μg boron/g cell protein).

Example 6

Intracellular Retention of BF

U343 mga cells, were plated on Petri dishes at 75% cell density and incubated with one of 1-4-dihydroxyboryl-phenylalanine (BPA) or BF in tissue culture medium for 18 hours. Both boronated compounds were added to the tissue culture medium at equimolar concentrations with respect to the boron content ($5 \times 10^{-4}$ M boron). Incubations were stopped by replacing the boron-containing medium with culture medium without boron. Cell samples were harvested at time points 0, 2 and 7 hours where the 0 time point represents immediate after 18 hour incubation of boronated compound.

Cells were washed with cold PBS and harvested by scraping them off the plastic dish using a rubber policeman, collected in cold PBS and pelleted by centrifugation. Cell pellets were analysed for total protein and boron content as described.

The results are shown in Table 3 below. Following intracellular uptake, BF was retained in tumour cells with 40% of the total uptake present 7 hours after total depletion of BF in the culture medium.

TABLE 3

Boron content (μg boron/g cell pellet) in U343mga cells at 0, 2 and 7 hours after withdrawal of boron containing medium.

| Boronated compound | 0 hour | 2 hours | 7 hours |
| --- | --- | --- | --- |
| BPA | 0.075 | 0 | 0 |
| BF | 0.79 | 0.59 | 0.3 |

The invention claimed is:

1. A compound according to formula (I)

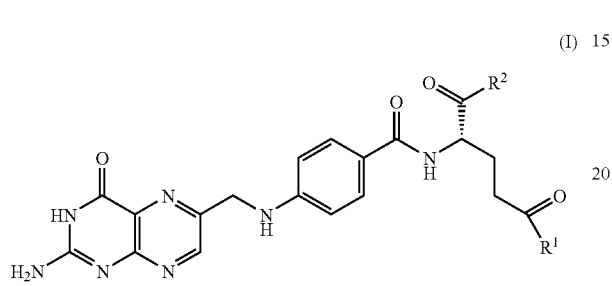

wherein one of $R^1$ and $R^2$ is —NH—X—Y—Z, —O—X—Y—Z or —S—X—Y—Z, and the other is —OH, —NH—X—Y—Z, —O—X—Y—Z or —S—X—Y—Z;

wherein

X is —$(CH_2)_m$—, wherein m is 0, 1, 2, 3 or 4, or —$(CH_2)_p$—O—$(CH_2)_q$—, wherein p and q independently are 1, 2, 3 or 4;

Y is a borane or a carborane, wherein at least one boron atom is $^{10}B$; and

Z is H or a hydrophilizing group, such as aminomethyl, 2-aminoethyl, 3-aminopropyl, 1,3-propanediol-2-yl-methoxyl, ethyleneglycoxyl or diethyleneglycoxyl;

and pharmaceutically acceptable salts and stereoisomers thereof.

2. The compound according to claim 1, wherein Y is

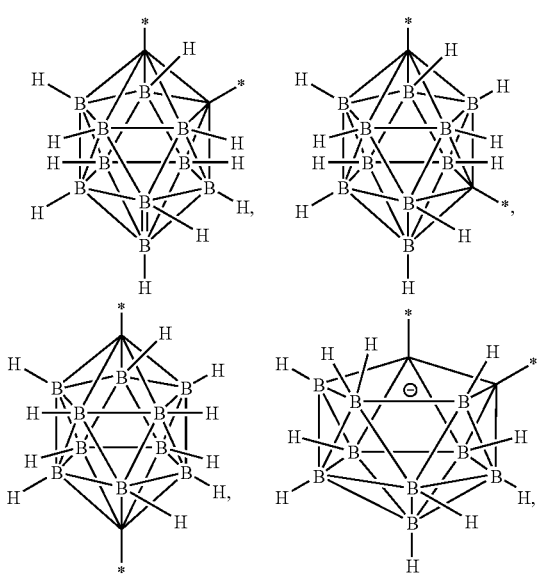

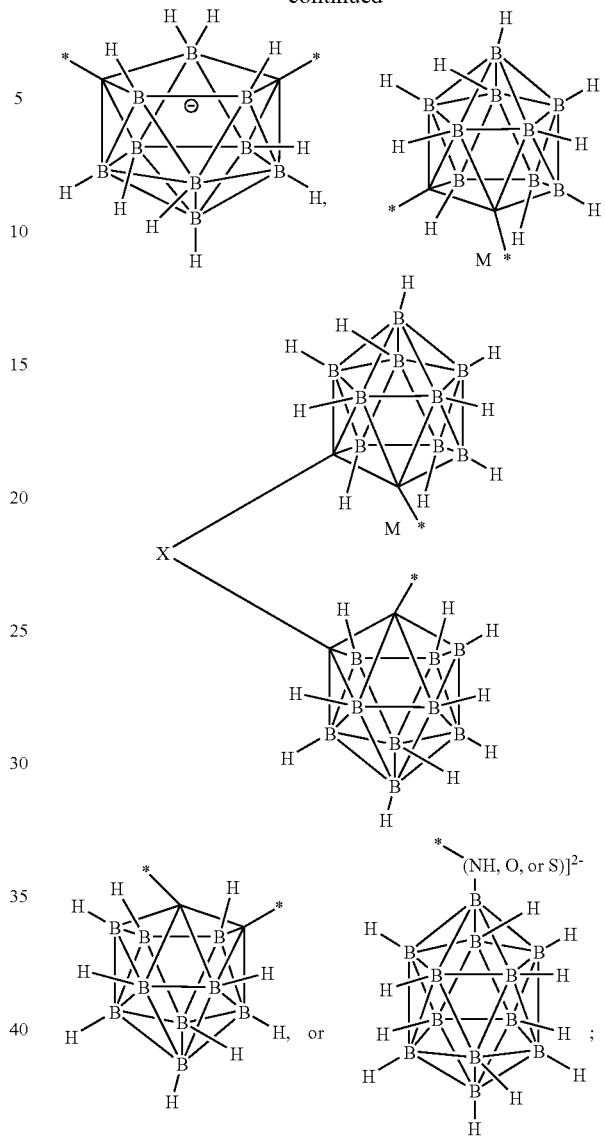

wherein

* indicates a location of a bond to X or Z;

M is cobalt, cobalt-57 or iron; and

X is as defined in claim 1.

3. The compound according to claim 2, which is $N^2$-(4-{[(2-amino-4-oxo-3,4-dihydropteridin-6-yl)methyl]amino}benzoyl)-N-{3-[(1R,9S)-2,3,4,5,6,7,8,10,11,12-decaborabicyclo[7.2.1]dodec-1-yl]propyl}-α-glutamine or $N^2$-(4-{[(2-amino-4-oxo-3,4-dihydropteridin-6-yl)methyl]amino}benzoyl)-N-[3-(2,3,4,5,6,7,8,10,11,12-decaborabicyclo[7.2.1]dodec-1-yl)propyl]-L-glutamine.

4. The compound according to claim 1, wherein $R^1$ is —NH—X—Y—Z, —O—X—Y—Z or —S—X—Y—Z, and $R^2$ is OH.

5. The compound according claim 1, wherein at least one carbon atom is $^{11}C$.

6. The compound according to claim 1 for use in therapy.

7. The compound according to claim 5 for use in diagnostics.

8. The pharmaceutical composition comprising the compound according to claim 1 and a pharmaceutically acceptable carrier, diluent or adjuvant.

9. A process for the preparation of the compound according to claim 1, comprising
reacting a compound of formula NH$_2$—X—Y—Z, OH—X—Y—Z or SH—X—Y—Z with folic acid, wherein X, Y and Z are as defined in claim 1.

10. A method of tumour therapy, comprising
administering a pharmaceutically and pharmacologically effective amount of the compound according to claim 1 to a subject in need thereof in conjunction with boron neutron capture therapy.

11. The method of tumour therapy according to claim 10, wherein the tumour originates from the central nervous system.

12. A method of tumour diagnostics, comprising
administering a pharmaceutically and pharmacologically effective amount of the compound as defined in claim 5 to a subject to be diagnosed in conjunction with positron emission tomography.

13. The method of tumour therapy according to claim 10, wherein the tumour is a glioma.

14. The method of tumour therapy according to claim 10, wherein the tumour is a glioblastoma, gliosarcoma, anaplastic astrocytoma, low grade astrocytoma, pilolytic astrocytoma, oligodendroglioma, brain stem glioma, meningioma, peripheral neuroepithelioma, primitive neuroectodermal tumour, neuroblastoma, germinoma, pituitary tumour, metastatic brain tumour, or arteriovenous malformation.

15. The method of tumour therapy according to claim 10, wherein the tumour is a malignant tumour or metastatic tumour process.

16. The method of tumour therapy according to claim 10, wherein the tumour is a melanoma, prostate cancer, hepatic cancer, lung cancer, breast cancer or sarcoma.

* * * * *